(12) United States Patent
Nenno et al.

(10) Patent No.: US 7,194,908 B2
(45) Date of Patent: Mar. 27, 2007

(54) DEVICE AND METHOD FOR ULTRASONIC INSPECTION USING PROFILOMETRY DATA

(75) Inventors: Thomas W. Nenno, Murrysville, PA (US); Patrick M. Minogue, Pittsburgh, PA (US); Rick D. Rishel, Monroeville, PA (US)

(73) Assignee: Westinghouse Electric Co. LLC, Pittsburgh, PA (US)

( * ) Notice: Subject to any disclaimer, the term of this patent is extended or adjusted under 35 U.S.C. 154(b) by 213 days.

(21) Appl. No.: 11/031,841

(22) Filed: Jan. 7, 2005

(65) Prior Publication Data

US 2005/0150300 A1    Jul. 14, 2005

Related U.S. Application Data

(60) Provisional application No. 60/535,313, filed on Jan. 9, 2004.

(51) Int. Cl.
*G01N 29/26* (2006.01)

(52) U.S. Cl. .............................. 73/618; 73/625; 73/628

(58) Field of Classification Search .................. 73/597, 73/602, 620, 627, 663, 618, 644, 622, 625, 73/628
See application file for complete search history.

(56) References Cited

U.S. PATENT DOCUMENTS

| 4,235,112 A | | 11/1980 | Kaiser |
| 4,559,825 A | | 12/1985 | Martens |
| 5,062,297 A | * | 11/1991 | Hashimoto et al. ............ 73/597 |
| 5,066,452 A | | 11/1991 | Hancock et al. |
| 5,161,413 A | * | 11/1992 | Junker et al. .................. 73/634 |
| 5,398,113 A | * | 3/1995 | de Groot ..................... 356/497 |
| 5,423,219 A | * | 6/1995 | Yaginuma et al. ........... 376/252 |
| 5,700,955 A | * | 12/1997 | Roth ............................ 73/597 |
| 5,757,502 A | | 5/1998 | Weling |

* cited by examiner

*Primary Examiner*—Hezron Williams
*Assistant Examiner*—Jacques M Saint-Surin

(57) ABSTRACT

An ultrasonic testing assembly structured to examine a test object, wherein the test object has a surface, and the examination examines the structure of the test object under the surface as well as the profile of the surface. The ultrasonic testing assembly includes a sled assembly structured to support a plurality of ultrasonic transducers, the sled assembly including at least one support member having a lower surface, at least one surface ultrasonic transducer coupled to the sled assembly and structured to extend below the support member lower surface and further structured to engage the test object surface, the surface ultrasonic transducer structured to examine internal structure of the test object and provide a first output, at least one profiling device coupled to the sled assembly, the profiling device structured to measure the profile of the test object surface and provide a second output, and a control device structured to correlate the first output and the second output and to calculate a corrected output.

23 Claims, 7 Drawing Sheets

DEVICE AND METHOD FOR ULTRASONIC INSPECTION USING PROFILOMETRY DATA

CROSS-REFERENCE TO RELATED APPLICATION

This application claims priority under 35 U.S.C. §119(e) to U.S. Provisional Patent Application Ser. No. 60/535,313, filed Jan. 9, 2004 entitled, THROUGHWALL SIZING USING PROFILOMETRY DATA.

BACKGROUND OF THE INVENTION

1. Field of the Invention

The present invention relates to a device and a method for ultrasonic inspection and, more specifically, to a device and a method for ultrasonic inspection wherein the device is structured to measure the profile of the object being tested and use that data to improve the results of the ultrasonic inspection device.

2. Background Information

The use of non-destructive inspection devices which utilize ultrasonic vibrations is well known. Generally, an ultrasonic transducer, typically a piezoelectric crystal which is excited by an electrical pulse, is placed on the surface of a test object. The transducer alternately sends an ultrasonic signal and receives an echo. The piezoelectric crystal converts vibrations from the echo back into an electrical signal which can be interpreted by a control device. The control device may record and/or display the interpreted signal. Where there is a variation of the internal structure of the test object, e.g. an internal crack within a metal member, the ultrasonic transducer and control device are able to provide an image showing the location and extent of the crack. The ultrasonic transducer and control device, however, suffer from limitations that affect the accuracy of the image.

For example, the ultrasonic transducer typically has a contact surface that engages the test object. The contact surface may have a cross-sectional area of about 0.50 square inches. The ultrasonic transducer contact surface should engage the test object in a generally flat manner and the test object should engage substantially all of the ultrasonic transducer contact surface. In this configuration, the distance the ultrasonic waves and echo travel can be determined and the control device may produce a substantially accurate representation of the test object's internal structure. However, where the test object surface is uneven, the signal/response time is affected and the control device may produce an inaccurate representation of the test object's internal structure. That is, as shown in FIG. 1, an ultrasonic transducer 1 with a contact surface 2 is disposed on the flat surface of a test object 3. The test object 3 has a defect 4 extending to a depth. The ultrasonic transducer 1 sends a signal and receives a response, represented by the arrow. It is noted that the signal may be directed at an angle relative to the contact surface 2. The response is created when the signal encounters the tip 5 of the defect 4. As the ultrasonic transducer 1 is moved toward the defect 4 additional responses are collected from the signal reflecting from other parts of the defect 4. The control device interprets this data as is known in the art and creates a representation of the defect 4 including the depth at the defect lower end 5. In this example, because the test object 3 surface 8 is flat, the actual depth and the apparent depth are the same.

However, as shown in FIG. 2, where the test object 3 surface is not flat, the actual depth and the apparent depth are the not the same. That is, as shown, the defect 4 is located in a depression 6. As shown, there is a gradual transition between the normal surface of the test object 3 and the depression 6. Thus, when the ultrasonic transducer 1 is disposed above the depression 6, the signal and echo will travel the distance from the normal test object 3 surface 8, as opposed to the depression 6 surface. Thus, the control device interprets this data as if the depression 6 did not exist and, as shown, the control device will show an apparent depth that is not the actual depth of the defect 4. As shown in FIG. 3, a similar error can occur when the ultrasonic transducer 1 is disposed on the transition part of the depression 6. In this instance, the angle of the ultrasonic transducer 1 on the transition portion creates a slanted path for the signal and echo which, in turn, creates an inaccurate reading. Further, as shown in FIG. 4, if the ultrasonic transducer 1 is disposed in the depression 6 and the defect 4 is located outside of the depression 6, the signal and echo travel a shorter distance than the actual depth of the defect 4. Again, the apparent depth of the defect 4 will be inaccurate.

As shown in FIGS. 5A and 5B, another type of error may occur as the ultrasonic transducer 1 is moved over an angle in the surface of the test object 3. That is, as noted above, the ultrasonic transducer 1 detects different parts of the defect 4 as the ultrasonic transducer 1 is moved. Thus, where a defect 4 does not extend to the surface, there may be an error as to where the defect 4 begins as well as where the defect 4 ends. That is, as shown in FIG. 5, the ultrasonic transducer 1 is disposed on the transition part of the depression 6. This creates an error, as noted above, in locating the depth of the lower end 5 of the defect 4. As the ultrasonic transducer 1 is moved toward the defect 4 as shown by ultrasonic transducer 1', and the ultrasonic transducer 1' is located over the vertex between the transition portion of the depression 6 and the bottom of the depression 6, the ultrasonic transducer contact surface 2' is spaced from the surface of the test object 3. Thus, for the reasons noted above, there is also an error in detecting the top end 7 of the defect 4. Thus as shown in FIG. 5B, the apparent depth of the defect 4 is not the same as the actual depth of the defect 4.

There is, therefore, a need for a device, and a method of using the device, to correct ultrasonic data based on variations in the profile of the test object 3.

There is a further need for a device, and a method of using the device, that measures the profile of a test object 3 during the ultrasonic examination.

SUMMARY OF THE INVENTION

These needs, and others, are met by the present invention which provides for an ultrasonic testing assembly structured to examine a test object, wherein the test object has a surface, and the examination examines the structure of the test object under the surface as well as the profile of the surface. The ultrasonic testing assembly includes a sled assembly structured to support a plurality of ultrasonic transducers, the sled assembly including at least one support member having a lower surface, at least one surface ultrasonic transducer coupled to the sled assembly and structured to extend below the support member lower surface and further structured to engage the test object surface, the surface ultrasonic transducer structured to examine internal structure of the test object and provide a first output, at least one profiling device coupled to the sled assembly, the profiling device structured to measure the profile of the test object surface and provide a second output, and a control device structured to utilize the information gathered from the profiling device to calculate a corrected output of the surface transducer.

The sled assembly is, preferably, a planar member having an opening for each ultrasonic transducer. The planar member may have additional openings, or brackets with openings attached thereto, so that other components may be coupled to the sled assembly. For example, a propulsion device, such as a robotic arm or a cable attached to a motor driven spool, may be attached to the sled assembly in order to move the sled assembly.

The at least one surface ultrasonic transducer extends through an opening in the sled assembly planar member and below the lower surface. The surface transducers are mounted on spring loaded compliance mechanisms which assure contact is maintained with the inspection object. Each surface ultrasonic transducer has a substantially planar contact surface structured to engage the test object. The surface ultrasonic transducer may be a single ultrasonic transducer that alternates sending and receiving an ultrasonic signal or echo. However, in the preferred embodiment, the at least one surface ultrasonic transducer includes two ultrasonic transducers, one to send a signal and one to receive the signal, also known as a "transmit-receive" or "pitch-catch" configuration. The at least one surface ultrasonic transducer may include additional single ultrasonic transducers, or pairs of ultrasonic transducers, as desired. Each surface ultrasonic transducer extends below the lower surface or the sled assembly and engages the test object. Each surface ultrasonic transducer produces an electrical output signal.

The profiling device may be any type of known profilometry device, such as a laser interferometry device, a laser triangulation device, or an atomic force microscopy device. However, in the preferred embodiment, the profiling device is an ultrasonic profilometry system. An ultrasonic profilometry system includes at least one profiling ultrasonic transducer that is coupled to the sled assembly in a known location relative to the at least one surface ultrasonic transducer. The at least one profiling ultrasonic transducer is coupled to the sled assembly so that there is a space between the surface of the test object and the at least one profiling ultrasonic transducer. In this manner, the at least one profiling ultrasonic transducer signal does not, substantially, penetrate the test object, but instead reflects off of the test object surface so that contour of the test object surface may be measured. Each profiling ultrasonic transducer produces an electrical output signal.

The control device is similar to those known in the art to the extent that the control device includes electronics structured to receive and interpret the output signals from the ultrasonic transducers. The control device is further structured to record and/or display the interpreted outputs, for example, but not limited to, on a display device such as a monitor. The control device is further structured, that is, it includes electronics designed to interpret the output from the profiling ultrasonic transducer and correct the surface ultrasonic transducer output based on the profile of the test object surface. In this manner, the ultrasonic testing assembly can be used to better determine the actual locations of defects and other internal structures within the test object.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

Figure 1:
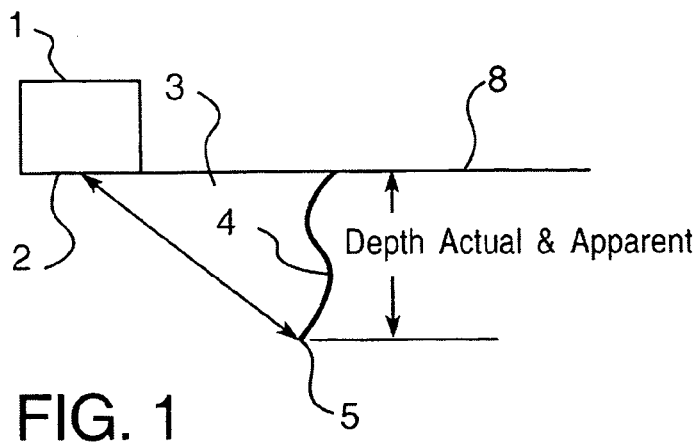
FIG. 1 is a schematic side view of the prior art ultrasonic transducer on a flat surface.
Figure 2:
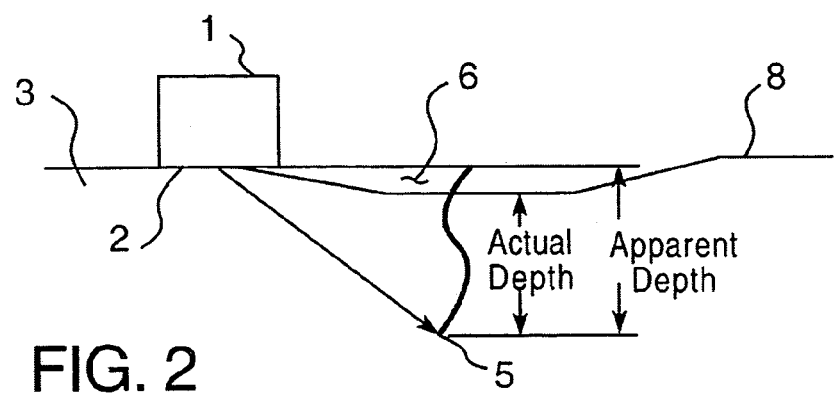
FIG. 2 is a schematic side view of the prior art ultrasonic transducer on an uneven surface.
Figure 3:
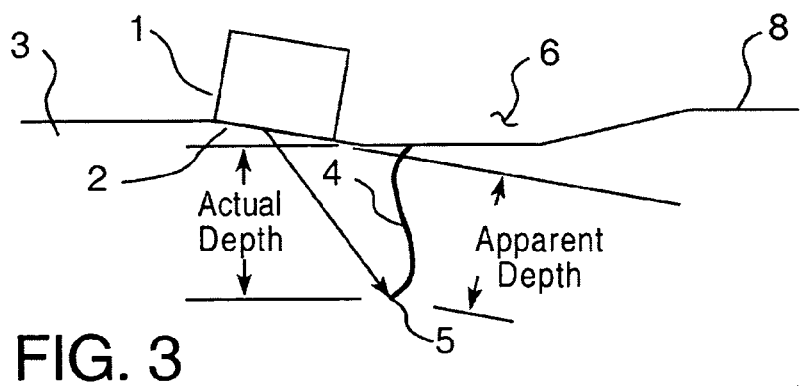
FIG. 3 is a schematic side view of the prior art ultrasonic transducer on an uneven surface.
Figure 4:
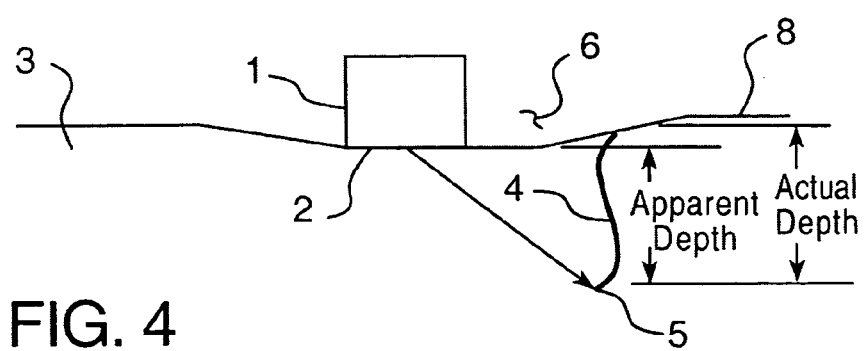
FIG. 4 is a schematic side view of the prior art ultrasonic transducer on an uneven surface.
Figures 5A, 5B:
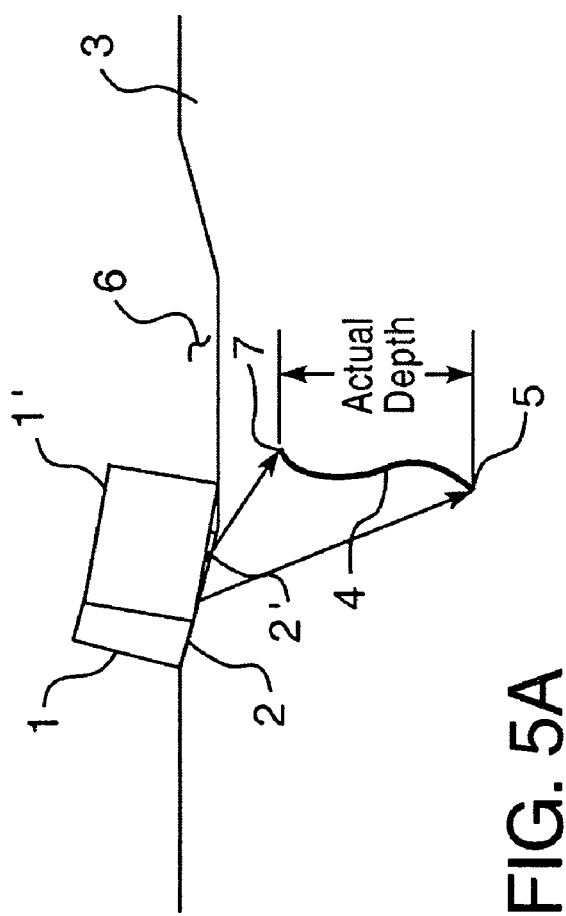
FIG. 5 is a schematic side view of the prior art ultrasonic transducer on an uneven surface.
Figure 6:
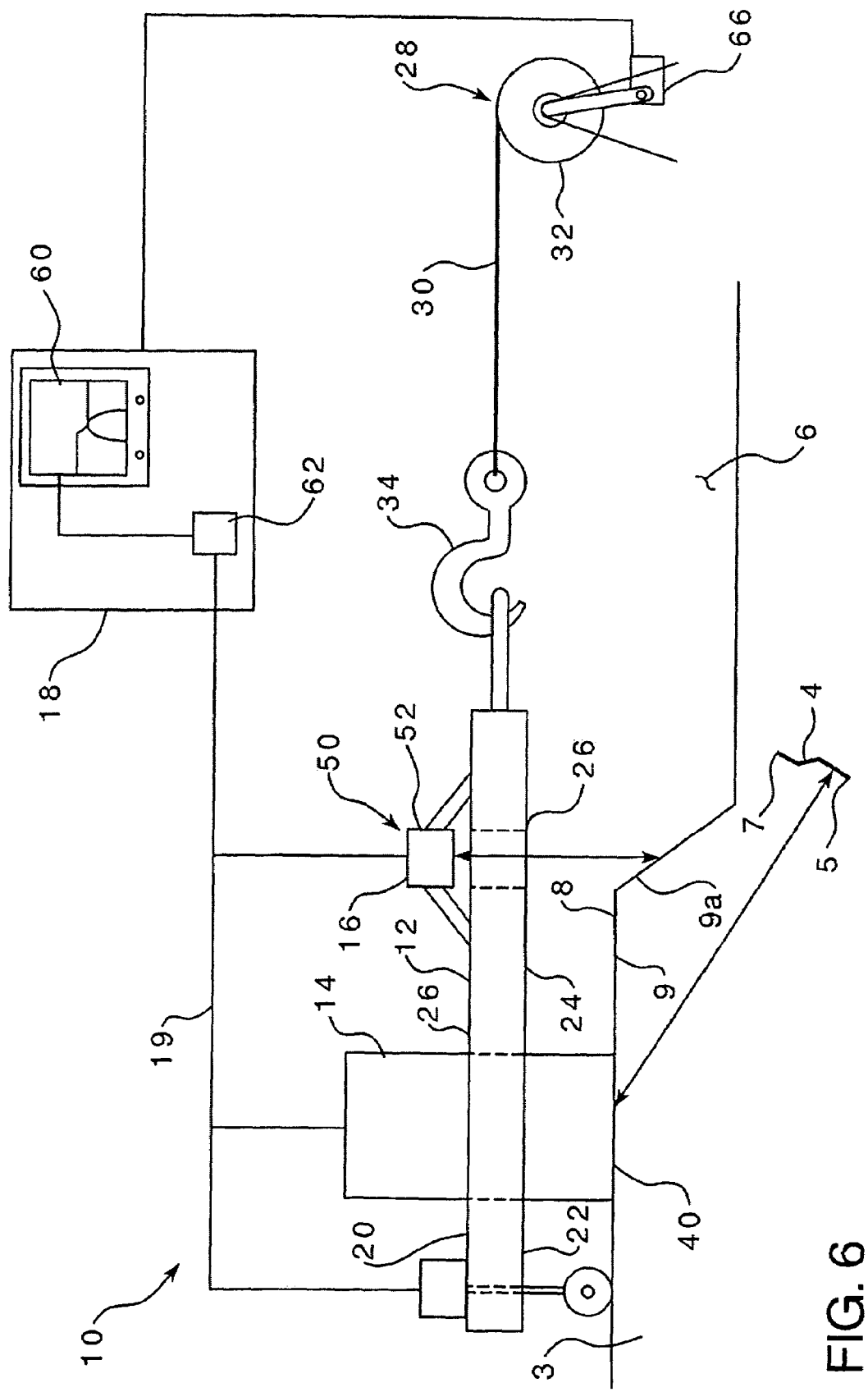
FIG. 6 is a schematic side view of an ultrasonic testing assembly according to the present invention having a single surface ultrasonic transducer and a single profiling ultrasonic transducer.

As shown in FIG. 6, and an alternate embodiment shown in FIG. 8 (discussed below), an ultrasonic testing assembly 10 is structured to examine a test object 3 having a surface 8. Within test object 3 there is a defect 4, e.g. a crack. The defect 4 has a lower end 5 and a top end 7. The surface 8 has a normal portion 9 and a depression 6 with a transition portion 9a therebetween. It is noted that the size of the depression 6 is exaggerated. The ultrasonic testing assembly 10 includes a sled assembly 12, at least one surface ultrasonic transducer 14, at least one profiling device 16, and a control device 18. The sled assembly 12 is structured to support a plurality of ultrasonic transducers or other components, including the at least one surface ultrasonic transducer 14, and at least one profiling device 16. The sled assembly 12 has at least one support member 20 having a lower surface 22. The at least one support member 20 may, for example, be a frame assembly (not shown), but in a preferred embodiment is a generally planar member 24 having a plurality of openings 26 therethrough. The sled assembly 12 may further include a propulsion device 28, such as, but not limited to, a cable 30 on a winch 32. The cable 30 may be coupled to the planar member 24 by a hook 34. The sled assembly 12 may also be moved by hand or the test object 3 may be moved under the sled assembly 12. The propulsion device 28 must have a feature that the positions of the transducer 14 and profiling device 16 relative to the test object 3 in a known orientation.

The at least one surface ultrasonic transducer 14 is coupled to the sled assembly 12 and structured to extend below the support member lower surface 22. The surface ultrasonic transducer 14 has a contact surface 40, which is generally flat, and which is structured to engage the test object surface 8. As is known in the art, the surface ultrasonic transducer 14 is structured to alternately send and receive an ultrasonic signal, as indicated by the forward sweeping arrow, and thereby examine internal structure of the test object 3. The received ultrasonic signal is converted to an electrical first output signal. The at least one surface ultrasonic transducer 14 extends through an opening 26 in the sled assembly planar member 24 and below the lower surface 22. As such, the surface ultrasonic transducer 14 is the lowest point on the ultrasonic testing assembly 10 and will engage the test object 3.

The least one profiling device 16 is also coupled to the sled assembly 12. The profiling device 16 is structured to measure the profile of the test object surface 8. The profiling device 16 may be any type of known profilometry device, such as a laser interferometry device, a laser triangulation device, or an atomic force microscopy device. However, in the preferred embodiment, the profiling device 16 is an ultrasonic profilometry system 50. An ultrasonic profilometry system 50 includes at least one profiling ultrasonic transducer 52 that is coupled to the sled assembly 12 in a known location relative to the at least on surface ultrasonic transducer 14. The at least one profiling ultrasonic transducer 52 is coupled to the sled assembly 12 so that there is a space between the test object surface 8 and the at least one profiling ultrasonic transducer 52. In this manner, the at least one profiling ultrasonic transducer 52 signal, as indicated by the generally vertical arrow, does not, substantially, penetrate the test object 3. Instead, the at least one profiling ultrasonic transducer 52 signal reflects off of the test object surface 8 so that contour of the test object surface 8 may be measured. Each profiling device 16 produces a second electrical output signal.

The control device 18 is structured to correlate the first output and the second output, calculate a corrected output, and record or display data representing the corrected output. The control device 18 is similar to those known in the art and includes electronics (not shown) structured to receive, via wires 19, and interpret the output signals from the at least one surface ultrasonic transducer 14 and at least one profiling device 16. The control device 18 is further structured to record and/or display the interpreted outputs, for example, but not limited to, on a display device such as a monitor 60. In a preferred embodiment, the control device 18 includes a three dimensional modeling device 62, and the corrected output is recorded and displayed as a three dimensional model. The control device 18 is further structured, that is, it includes electronics designed to interpret the output from the profiling device 16 and correct the surface ultrasonic transducer 14 output based on the profile of the test object surface 8. The correction is performed using calculations known in the art, for example, but not limited to, Snell's Law. In this manner, the ultrasonic testing assembly 10 can be used to better determine the actual locations of defects and other internal structures within the test object 3.

Figure 9:
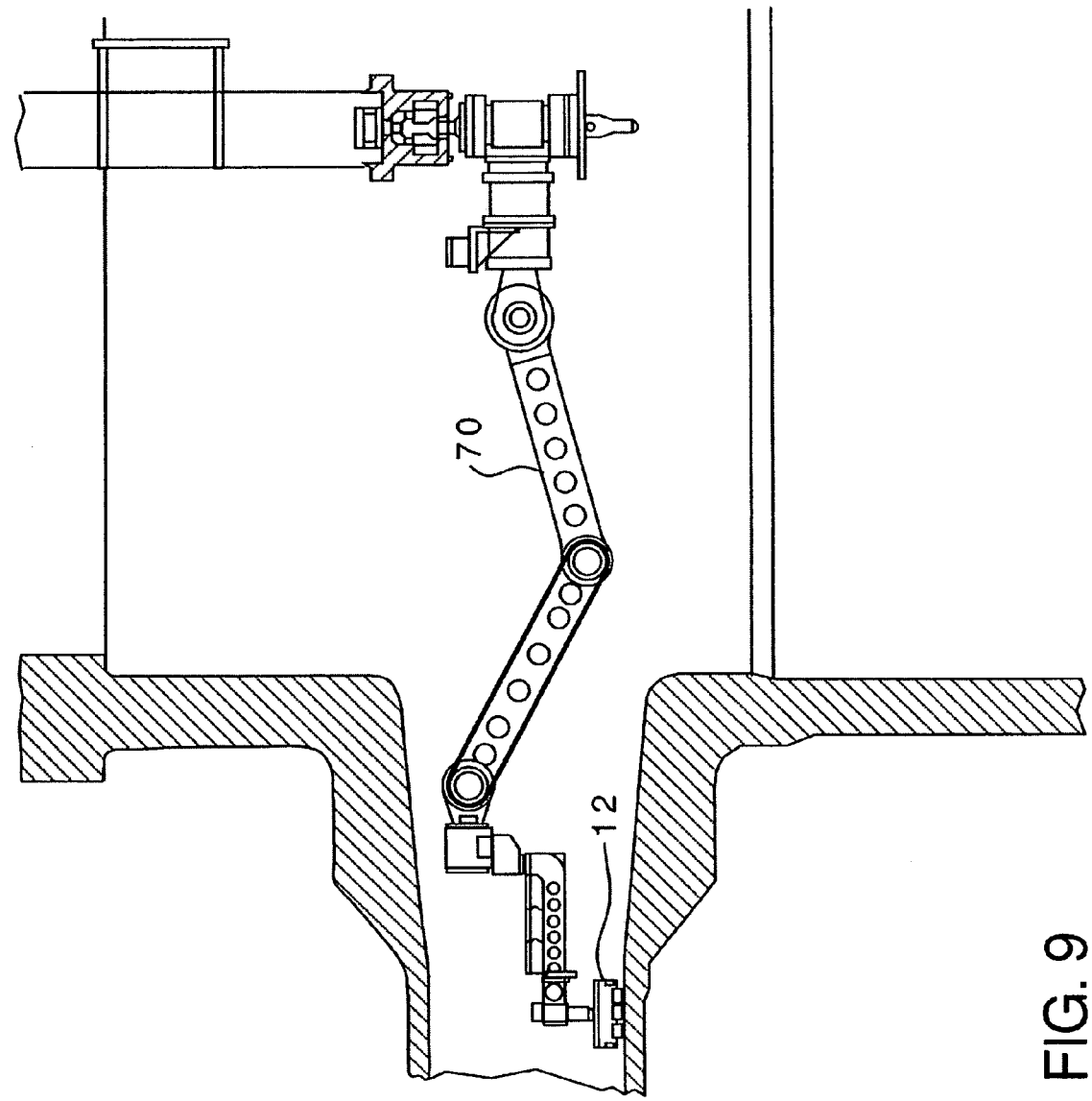
FIG. 9 is a side view of a robotic arm supporting the ultrasonic testing assembly.

The ultrasonic testing assembly 10 may track the location of surface changes by various techniques. For example, in one embodiment, the profiling device 16 is disposed on the sled assembly 12 in a predetermined relationship to the at least one surface ultrasonic transducer 14, preferably adjacent to the surface ultrasonic transducer 14. Additionally, the propulsion device 28 is structured to move the sled assembly 12 at a predetermined speed, or the propulsion device 28 may include a device 66 to monitor the speed of the sled assembly 12 movement. In a preferred embodiment, as shown in FIG. 9, the sled assembly 12 is coupled to a robotic arm 70. As is known in the art, the robotic arm 70, includes a monitoring device 66 in the form of encoders or resolvers, typically located at each joint in the robotic arm 70. The data from monitoring device 66 is converted to a third electrical signal. The control device 18 is programmed with, or collects the third signal data, and incorporates the data into the calculation of the corrected output. That is, the control device may determine which part of the profile of the surface 8 the surface ultrasonic transducer 14 is located.

Figure 7:
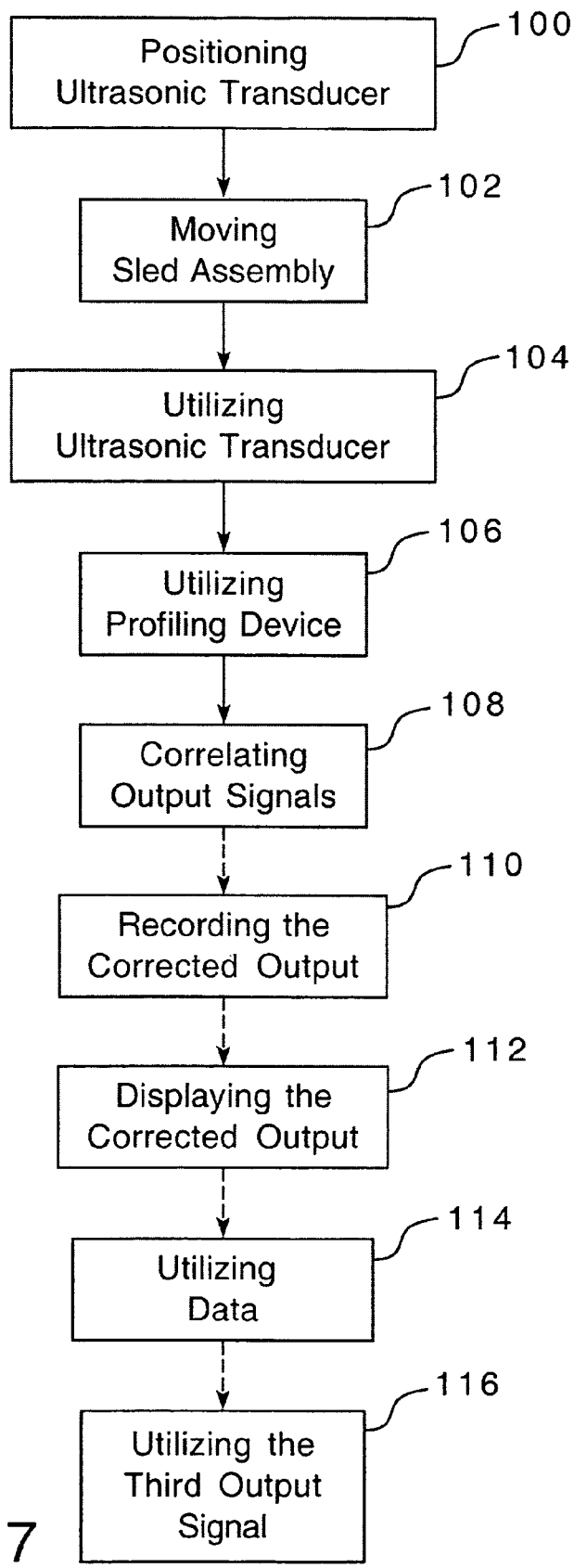
FIG. 7 is a flowchart of the steps of the method of using the ultrasonic testing assembly.

Thus, as shown on FIG. 7, using the ultrasonic testing assembly 10 described above, the method of examining the interior structure of a test object 3 includes the steps of: positioning 100 the at least one surface ultrasonic transducer against the test object 3, moving 102 the sled assembly 12 along the surface of the test object 3, utilizing 104 the at least one surface ultrasonic transducer 14 to create a first output signal representing the interior structure of the test object 3, utilizing 106 the profiling device 16 to measure any changes in the surface of the test object 3 and creating a second output signal, correlating 108 the first output and the second output and to calculate a corrected output representing the interior structure of the test object 3. Further, the method may include the steps of recording 110 and/or displaying 1112 the corrected output as a three dimensional model. The method may also include a step of utilizing 114 the data representing the speed of the sled assembly 12 and the positioning of the at least one surface ultrasonic transducer 14 and the at least one profiling device 16 in the comparison of the first and second output signals, or a step of utilizing 116 the third output signal in the step of correlating the first output and the second output and to calculate a corrected output representing the interior structure of the test object 3.

Figure 10:
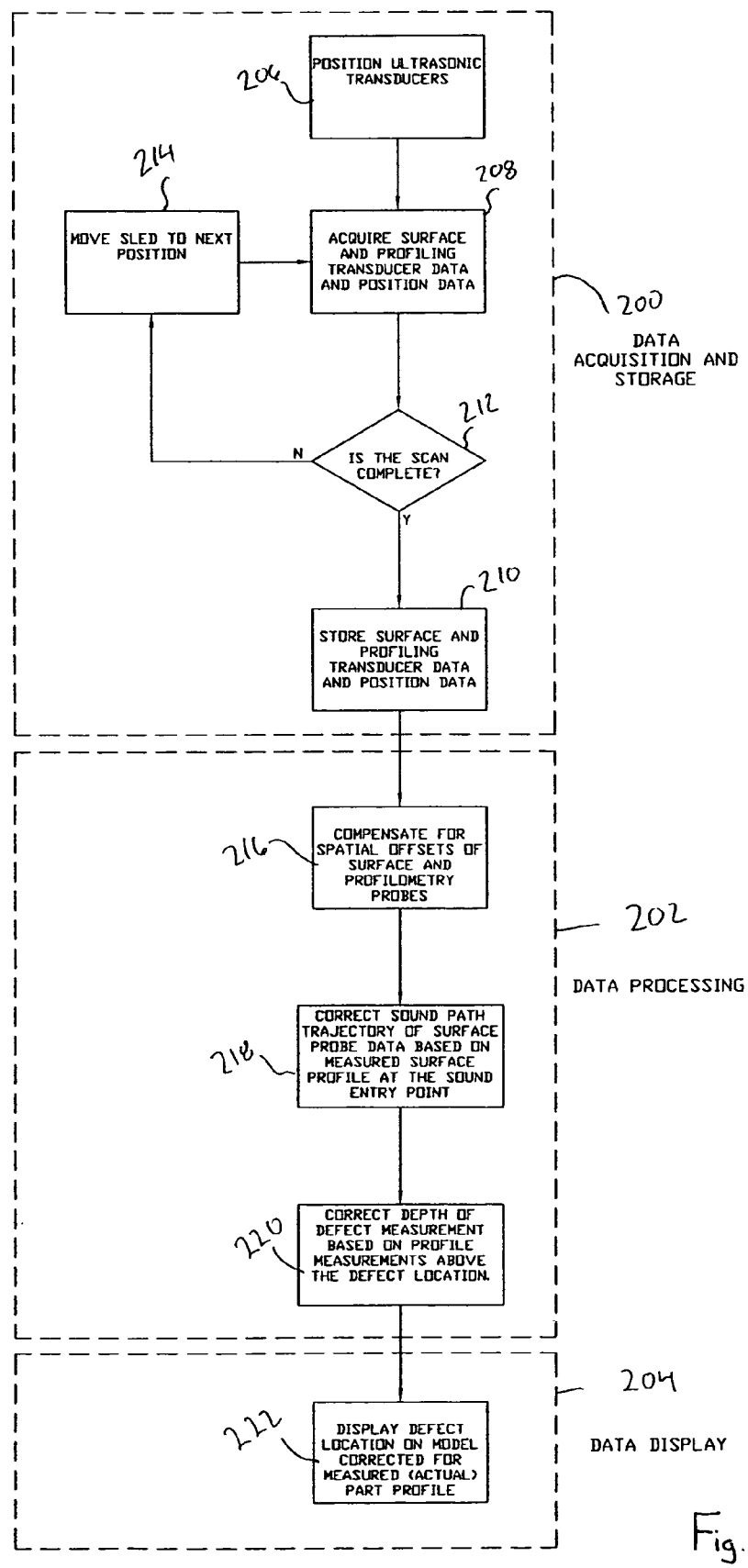
FIG. 10 is an alternate flowchart of the steps of the method of using the ultrasonic testing assembly.

FIG. 10 shows an alternate embodiment of the steps of the method of using the present invention. Generally, there are three steps for receiving data from the ultrasonic testing assembly 10, a step of acquiring and storing 200 data, a step of processing 202 the data, and a step of displaying 204 the data. The step of acquiring and storing 200 data includes the steps of positioning 206 the sled assembly 12 having the surface ultrasonic transducer 14 and at least one profiling device 16, acquiring 208 surface and profile data, and storing 210 the surface and profile data. The step of acquiring and storing 200 data may include the additional steps of deciding 212 whether the scan is complete and, if not, moving the sled assembly 12 to another position.

The step of processing 202 the data includes the steps of compensating 216 for the spatial offsets of the surface ultrasonic transducer 14 and at least one profiling device 16, correcting 218 the sound path of the surface ultrasonic transducer 14 based on the surface profile at the sound entry point as determined by at least one profiling device 16, and correcting 220 the depth of the defect measurement as determined by the surface ultrasonic transducer 14 based on the profile measurements of the defect location. The step of displaying 204 the data includes the step of displaying 222 the defect location on a model corrected for the measure part profile.

Figure 8:
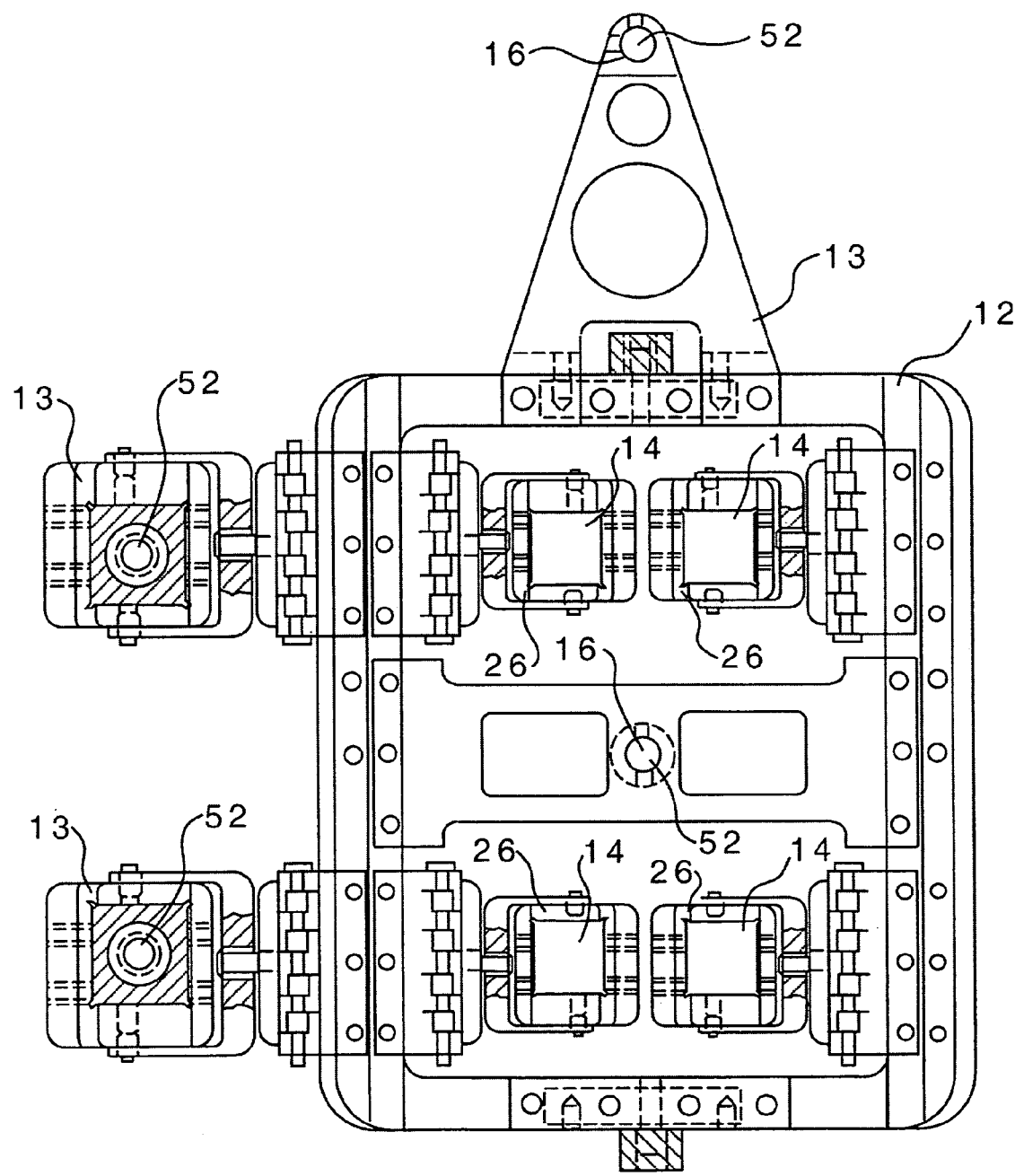
FIG. 8 is a top view of an ultrasonic testing assembly according to the present invention having multiple surface ultrasonic transducers and multiple profiling ultrasonic transducers.

FIG. 8 shows a more complex version of the ultrasonic testing assembly 10. In this embodiment, the sled assembly 12 includes openings 26 for multiple ultrasonic transducers as well as a plurality of attached brackets 13. The sled assembly 12 has multiple profiling devices 16, which are preferably profiling ultrasonic transducers 52, as well as multiple surface ultrasonic transducers 14. The surface ultrasonic transducers 14 operate in pairs, one surface ultrasonic transducer 14 sending an ultrasonic signal and the other surface ultrasonic transducer 14 receiving the ultrasonic signal. The control device 18 is structured to gather and combine data from all the ultrasonic transducers 14, 52 to create the corrected output.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

What is claimed is:

1. An ultrasonic testing assembly structured to examine a test object having a surface, including the structure of the test object under said surface, said ultrasonic testing assembly comprising:
   a sled assembly structured to support a plurality of ultrasonic transducers, said sled assembly including at least one support member having a lower surface;
   at least one surface ultrasonic transducer coupled to said sled assembly and structured to extend below said support member lower surface and further structured to engage said test object surface, said surface ultrasonic transducer structured to examine internal structure of said test object and provide a first output;
   at least one profiling device coupled to said sled assembly, said profiling device structured to measure the profile of said test object surface and provide a second output; and
   a control device structured to correlate said first output and said second output and to calculate a corrected output.

2. The ultrasonic testing assembly of claim 1 wherein said control device includes a recording device and said corrected output is recorded.

3. The ultrasonic testing assembly of claim 1 wherein said control device includes a recording device and a display device, and said corrected output is recorded and displayed.

4. The ultrasonic testing assembly of claim 1 wherein said control device includes a recording device, a display device, and a three dimensional modeling device, said corrected output is recorded and displayed as a three dimensional model.

5. The ultrasonic testing assembly of claim 1 wherein:
   said at least one profiling device is at least one profiling ultrasonic transducer, said profiling ultrasonic transducer coupled to said sled assembly so that said profiling ultrasonic transducer is spaced above said test object surface.

6. The ultrasonic testing assembly of claim 5 wherein said at least one profiling ultrasonic transducer is disposed adjacent to said at least one surface ultrasonic transducer.

7. An ultrasonic testing assembly structured to examine a test object having a surface, including the structure of the test object under said surface, said ultrasonic testing assembly comprising:
   a sled assembly structured to support a plurality of ultrasonic transducers, said sled assembly including at least one support member having a lower surface;
   at least one surface ultrasonic transducer coupled to said sled assembly and structured to extend below said support member lower surface and further structured to engage said test object surface, said surface ultrasonic transducer structured to examine internal structure of said test object and provide a first output;
   at least one profiling device coupled to said sled assembly, said profiling device structured to measure the profile of said test object surface and provide a second output;
   a control device structured to correlate said first output and said second output and to calculate a corrected output; and
   said sled assembly includes a propulsion device structured to move said sled assembly at a predetermined speed;
   said sled assembly is further structured to position said at least one surface ultrasonic transducer and said at least one profiling device in a predetermined relationship;
   said control device structured to include data representing said speed of said sled assembly and said positioning of said at least one surface ultrasonic transducer and said at least one profiling device in comparison of said first and second output signals, whereby the profile of the surface at the location that said at least one surface ultrasonic transducer is engaging may be factored into said corrected output.

8. An ultrasonic testing assembly structured to examine a test object having a surface, including the structure of the test object under said surface, said ultrasonic testing assembly comprising:
   a sled assembly structured to support a plurality of ultrasonic transducers, said sled assembly including at least one support member having a lower surface;
   at least one surface ultrasonic transducer coupled to said sled assembly and structured to extend below said support member lower surface and further structured to engage said test object surface, said surface ultrasonic transducer structured to examine internal structure of said test object and provide a first output;
   at least one profiling device coupled to said sled assembly, said profiling device structured to measure the profile of said test object surface and provide a second output;
   a control device structured to correlate said first output and said second output and to calculate a corrected output,
   said sled assembly includes a speed monitoring device structured to provide a third output signal;
   said sled assembly is further structured to position said at least one surface ultrasonic transducer and said at least one profiling device in a predetermined relationship; and
   said control device structured is further structured to record said third output signal and include data representing said positioning of said at least one surface ultrasonic transducer and said at least one profiling device in comparison of said first and second output signals, whereby the profile of the surface at the location that said at least one surface ultrasonic transducer is engaging may be factored into said corrected output.

9. The ultrasonic testing assembly of claim 1 wherein said at least one surface ultrasonic transducer and said at least one profiling device are structured to operate in a liquid medium.

10. A method of examining the interior structure of a test object using an ultrasonic testing assembly wherein the ultrasonic testing assembly comprises a sled assembly structured to support a plurality of ultrasonic transducers, said sled assembly including at least one support member having a lower surface, at least one surface ultrasonic transducer coupled to said sled assembly and structured to extend below said support member lower surface and further structured to engage said test object surface, said surface ultrasonic transducer structured to examine internal structure of said test object and provide a first output, at least one profiling device coupled to said sled assembly, said profiling device structured to measure the profile of said test object surface and provide a second output and a control device structured to correlate said first output and said second output and to calculate a corrected output, wherein said method comprises the steps of:
   positioning said at least one surface ultrasonic transducer against said test object;

moving said sled assembly along the surface of said test object;

utilizing said at least one surface ultrasonic transducer to create an output signal representing the interior structure of said test object;

utilizing said profiling device to measure any changes in the surface of said test object;

correlating said first output and said second output and to calculate a corrected output representing the interior structure of said test object.

11. The method of claim 10 wherein said control device includes a recording device and said corrected output is recorded and said method includes the step of recording said corrected output.

12. The method of claim 10 wherein said control device includes a recording device and a display device, and said method includes the step of recording and displaying said corrected output.

13. The method of claim 10 wherein said control device includes a recording device, a display device, and a three dimensional modeling device, and said method includes the step of displaying said interior structure as a three dimensional model.

14. The method of claim 10 wherein said at least one profiling device is at least one profiling ultrasonic transducer, said profiling ultrasonic transducer coupled to said sled assembly so that said profiling ultrasonic transducer is spaced above said test object surface.

15. The method of claim 14 wherein said at least one profiling ultrasonic transducer is disposed adjacent to said at least one surface ultrasonic transducer.

16. The method of claim 10 wherein said sled assembly is further structured to position said at least one surface ultrasonic transducer and said at least one profiling device in a predetermined relationship, and said control device is structured to include data representing said speed of said sled assembly and said positioning of said at least one surface ultrasonic transducer and said at least one profiling device in comparison of said first and second output signals, and said method includes the step of utilizing said data representing said speed of said sled assembly and said positioning of said at least one surface ultrasonic transducer and said at least one profiling device in comparison of said first and second output signals.

17. The method of claim 10 wherein said sled assembly includes a distance measurement device structured to provide a third output signal, said sled assembly is further structured to position said at least one surface ultrasonic transducer and said at least one profiling device in a predetermined relationship, said control device structured to record said third output signal and include data representing said positioning of said at least one surface ultrasonic transducer and said at least one profiling device in comparison of said first and second output signals, and said method includes the step of utilizing said third output signal in said step of correlating said first output and said second output and to calculate a corrected output representing the interior structure of said test object.

18. The method of claim 10 wherein said at least one surface ultrasonic transducer and said at least one profiling device are structured to operate in a liquid medium.

19. A method of examining the interior structure of a test object using an ultrasonic testing assembly wherein the ultrasonic testing assembly comprises a sled assembly structured to support a plurality of ultrasonic transducers, said sled assembly including at least one support member having a lower surface, at least one surface ultrasonic transducer coupled to said sled assembly and structured to extend below said support member lower surface and further structured to engage said test object surface, said surface ultrasonic transducer structured to examine internal structure of said test object and provide a first output, at least one profiling device coupled to said sled assembly, said profiling device structured to measure the profile of said test object surface and provide a second output and a control device structured to correlate said first output and said second output and to calculate a corrected output, wherein said method comprises the steps of:

acquiring and storing data;

processing the data, including the step of correcting the depth of the defect measurement as determined by the surface ultrasonic transducer based on the profile measurements of the defect location; and displaying the data.

20. The method of claim 19 wherein said step of processing the data includes the further steps of:

compensating for the spatial offsets of the surface ultrasonic transducer and at least one profiling device; and correcting the sound path of the surface ultrasonic transducer based on the surface profile at the sound entry point as determined by at least one profiling device.

21. The method of claim 19 wherein said step of acquiring and storing data includes the further steps of:

positioning the sled assembly having the surface ultrasonic transducer and at least one profiling device;

acquiring surface and profile data; and storing the surface and profile data.

22. The method of claim 21 wherein said step of acquiring and storing data includes the further steps of:

deciding whether the scan is complete; and, if not, moving the sled assembly to another position.

23. The method of claim 21 wherein said step of processing the data includes the further steps of:

compensating for the spatial offsets of the surface ultrasonic transducer and at least one profiling device; and correcting the sound path of the surface ultrasonic transducer based on the surface profile at the sound entry point as determined by at least one profiling device.

* * * * *